(12) United States Patent
Freifeid

(10) Patent No.: US 8,811,691 B2
(45) Date of Patent: Aug. 19, 2014

(54) STENT INSPECTION SYSTEM

(75) Inventor: Daniel Freifeid, Napa, CA (US)

(73) Assignee: Visicon Inspection Technologies LLC, Napa, CA (US)

( * ) Notice: Subject to any disclaimer, the term of this patent is extended or adjusted under 35 U.S.C. 154(b) by 1482 days.

(21) Appl. No.: 12/303,435

(22) PCT Filed: Jun. 5, 2007

(86) PCT No.: PCT/US2007/070399
§ 371 (c)(1),
(2), (4) Date: Jul. 15, 2009

(87) PCT Pub. No.: WO2007/143647
PCT Pub. Date: Dec. 13, 2007

(65) Prior Publication Data
US 2010/0014747 A1  Jan. 21, 2010

Related U.S. Application Data

(60) Provisional application No. 60/811,341, filed on Jun. 5, 2006.

(51) Int. Cl.
G06K 9/00 (2006.01)
A61F 2/04 (2013.01)

(52) U.S. Cl.
USPC ........... 382/128; 382/152; 623/23.7; 623/1.1; 623/1.15; 73/865.8

(58) Field of Classification Search
USPC ......... 382/128, 141, 152, 153, 154, 287, 294; 623/1.1, 1.15, 1.16, 1.17, 1.19, 23.7; 600/407, 410; 73/865.8; 348/45, 65, 86
See application file for complete search history.

(56) References Cited

U.S. PATENT DOCUMENTS

| 6,160,409 A * | 12/2000 | Nurioka ..................... 324/754.1 |
| 6,389,310 B1 * | 5/2002 | Demonceau et al. ......... 600/512 |
| 6,825,680 B1 * | 11/2004 | Kogan et al. ............. 324/750.19 |
| 7,209,575 B2 * | 4/2007 | Spaeth .......................... 382/103 |

(Continued)

OTHER PUBLICATIONS

Fessler (Nov. 2009) "analytical tomographic image reconstruction methods" pp. 1-47.*

(Continued)

Primary Examiner — Chan Park
Assistant Examiner — Mia M Thomas
(74) Attorney, Agent, or Firm — Wiggin and Dana LLP; Gregory S. Rosenblatt

(57) ABSTRACT

Apparatus, systems, and methods for inspecting longitudinal surfaces and sidewalls of cut tubes are disclosed. In some embodiments, the apparatus includes a line camera, the line camera being configured to capture images of longitudinal surfaces of the cut tubes, an area camera joined with the line camera, the area camera being configured to capture images of sidewalls of the cut tubes, a mandrel and drive, a multi-axis motion stage, a vertical motion stage, and a rotating motion stage. In some embodiments, the system includes a camera module, a tube positioning module, a motion control module, and an analysis module. In some embodiments, the method includes positioning a line and area cameras, moving the cut tubes, capturing images of the longitudinal surfaces and sidewalls of the cut tubes, providing comparable images of a template cut tube, and comparing the images of the cut tubes to those of the template cut tube.

13 Claims, 6 Drawing Sheets

(56) References Cited

U.S. PATENT DOCUMENTS

| | | | |
|---|---|---|---|
| 7,236,625 B2* | 6/2007 | Engelbart et al. | 382/141 |
| 7,313,263 B2* | 12/2007 | Mizutori et al. | 382/151 |
| 7,925,075 B2* | 4/2011 | Jia et al. | 382/149 |
| 8,081,307 B2* | 12/2011 | Cameron et al. | 356/237.1 |
| 8,134,700 B2* | 3/2012 | Cameron et al. | 356/237.1 |
| 2001/0037694 A1* | 11/2001 | Freifeld | 73/865.8 |
| 2002/0009217 A1* | 1/2002 | Bickert et al. | 382/141 |
| 2002/0024300 A1* | 2/2002 | Ferenc | 313/523 |
| 2002/0191836 A1* | 12/2002 | Freifeld | 382/152 |
| 2003/0223632 A1* | 12/2003 | Freifeld | 382/152 |
| 2004/0041904 A1* | 3/2004 | Lapalme et al. | 348/14.08 |
| 2005/0012817 A1* | 1/2005 | Hampapur et al. | 348/143 |
| 2005/0107688 A1* | 5/2005 | Strommer | 600/424 |
| 2005/0201838 A1* | 9/2005 | Wendzina et al. | 408/204 |
| 2005/0259863 A1* | 11/2005 | Freifeld | 382/152 |
| 2006/0126061 A1* | 6/2006 | Kreckel et al. | 356/241.1 |
| 2007/0078466 A1* | 4/2007 | Bodduluri et al. | 606/133 |
| 2007/0167710 A1* | 7/2007 | Unal et al. | 600/407 |
| 2007/0184422 A1* | 8/2007 | Takahashi | 434/262 |
| 2008/0144918 A1* | 6/2008 | Li et al. | 382/141 |
| 2009/0079728 A1* | 3/2009 | Sugita et al. | 345/418 |
| 2009/0251535 A1* | 10/2009 | Maehringer-Kunz et al. | 348/86 |
| 2010/0014747 A1* | 1/2010 | Freifeld | 382/141 |
| 2010/0262230 A1* | 10/2010 | Vecerina et al. | 623/1.46 |
| 2010/0309307 A1* | 12/2010 | Jin | 348/86 |
| 2011/0007147 A1* | 1/2011 | Cameron et al. | 348/92 |
| 2012/0013732 A1* | 1/2012 | Cameron et al. | 348/92 |

OTHER PUBLICATIONS

Gonzalo (Feb. 2010) "optical coherence tomography for the assessment of coronary atherosclerosis and vessel response after stent implantation" pp. 1-413.*

Pacakard (Jul. 2009) "the x rendering extension" pp. 1-15.*

Abbey (Aug. 2008) "perceptual assessment of multiple stent deployment" pp. 1-8.*

* cited by examiner (A)

(B)

(C)

STENT INSPECTION SYSTEM

CROSS REFERENCE TO RELATED APPLICATION(S)

This application claims the benefit of U.S. Provisional Application No. 60/811,341, filed Jun. 5, 2006, which is incorporated by reference as if disclosed herein in its entirety.

BACKGROUND

Stents are small, intricately cut tubes, generally made of materials such as stainless steel. Cardiovascular stents are permanently placed in a blood vessel to act as scaffolding to keep an occluded artery open. In use, cardiovascular stents are inserted into the artery on a catheter and are typically deployed by expanding a very small balloon at the end of the catheter upon which the stent is mounted.

Cardiovascular stents must meet stringent requirements to work properly. If the stent contains any rough or sharp edges, it will damage blood cells or the blood vessel in which it is inserted. This can lead to further atherosclerotic plaquing, emboli or thrombi, and result in potentially life threatening situations.

Lasers are typically used to cut stents. This process, while highly precise, can occasionally produce defective parts. Stents tend to be small, with diameters approximating 1 mm. After processing, the individual cut features on a stent range from 50 to 200 microns in size. Accordingly, small changes in manufacturing process parameters such as laser power, tubing diameter, or mechanical jitter can cause defects. Such defects may include an out of tolerance feature size or a malformed feature.

Since stents are used in the heart and other critical areas of blood flow, a failure in the function of the stent could be life threatening. Thus, manufacturers of stents typically employ 100% inspection procedures. A human operator utilizing a 50× optical power stereomicroscope typically inspects for visual defects. Dimensional inspection is typically done by a human operator utilizing a profile projector. Alternatively, this inspection can be done automatically by utilizing a vision system.

The problems associated with either the manual or the automatic approaches to inspection are numerous. First, human error makes visual inspection of products less than completely effective. In addition, such manual inspection is relatively slow and thus a relatively costly aspect of the manufacturing process. Furthermore, the pass/fail criteria of the profile projector using overlays, as is typically employed in manual inspection, does not generally provide any numeric dimensional data that would otherwise be useful for process control.

Stents are typically highly polished and have a very convoluted geometry with many intricate shapes. One ideal approach in inspection work is to compare the as-found geometry to the nominal or CAD model. While there are many practical commercial embodiments of systems to make this sort of inspection on generally rigid parts, these systems are not practical for the flexible stents.

CAD models are typically only available that represent the part ready for final inspection. It would be helpful for process control to have a means of creating a CAD model at different steps along the production cycle and have that model available for in-process inspection.

A means to image the highly contoured features that are part of the stent geometry has not been found. While methods are known for imaging the outside and the inside of stents, there has not been developed a practical method for imaging the sidewalls of these cut metal tubes, especially when the spacing between the cuts are narrow. In addition, a means has not been demonstrated to utilize a line scan camera with stents of any geometry except cylindrical.

SUMMARY

Apparatus for capturing images of longitudinal surfaces and sidewalls of cut tubes are disclosed. In some embodiments, the apparatus include the following: a line camera, the line camera being configured to capture images of longitudinal surfaces of the cut tubes; a rotatable, 360 degree area camera joined with the line camera, the area camera being configured to capture images of sidewalls of the cut tubes; a mandrel and drive adapted to hold and axially rotate the cut tubes about a Y-axis for positioning the cut tubes with respect to the line camera and the area camera; a multi-axis motion stage for moving the mandrel, drive, and cut tubes along an X-axis and along the Y-axis for positioning the mandrel, drive, and cut tubes with respect to the line camera and the area camera; a vertical motion stage for moving the line camera and the area camera along a Z-axis for positioning the line camera and the area camera with respect to the cut tubes; and a rotating motion stage for rotating the line camera and the area camera substantially about an X'-axis for positioning the line camera and the area camera with respect to the cut tubes.

Systems for inspecting longitudinal surfaces and sidewalls of cut tubes are disclosed. In some embodiments, the systems includes the following: a camera module including a line camera and a rotatable, 360 degree area camera, the line camera being configured to capture images of longitudinal surfaces of the cut tubes and the area camera being configured to capture images of sidewalls of the cut tubes; a tube positioning module including a mandrel and drive adapted to hold and axially rotate the cut tubes about a first axis, a multi-axis motion stage for moving the mandrel, drive, and cut tubes along the first axis and along a second axis, and a vertical motion stage for moving the line camera and the area camera along a Z-axis; a motion control module for controlling the multi-axis motion stage and the vertical motion stage to position the cut tubes with respect to the line and area cameras; and an analysis module for comparing the images of the longitudinal surfaces and sidewalls of the cut tubes to images of longitudinal surfaces and sidewalls of a template cut tube.

Methods of inspecting longitudinal surfaces and sidewalls of cut tubes are disclosed. In some embodiments, the methods include the following: positioning a line camera and an area camera for capturing images of the cut tubes; moving the cut tubes with respect to the line and area cameras for capturing images of the cut tubes; capturing images of the longitudinal surfaces of the cut tubes using the line camera; capturing images of the sidewalls of the cut tubes using the area camera; providing images of the sidewalls and longitudinal surfaces of a template cut tube; placing warp gauges at positions on the sidewalls and longitudinal surfaces of the template cut tube; generating difference vectors between the positions of the warp gauges and comparable positions of the captured images of longitudinal surfaces and sidewalls of the cut tubes; modifying edge points of longitudinal surfaces and sidewalls of the cut tubes based on a weighted average of a nearest warp gauge thereby generating warped images of the sidewalls and longitudinal surfaces of the cut tubes; and comparing the warped images of longitudinal surfaces and sidewalls of the cut tubes to the images of the sidewalls and longitudinal surfaces of the template cut tube.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Generally, the disclosed subject matter relates to apparatus, systems, and methods for inspection of cut tubes such as stents. A plurality of cameras and positioning stages are used to capture various images of the longitudinal surfaces and sidewalls of the stent. The captured images are compared to template images, e.g., a computer aided drafting (CAD) model, of an "ideal" stent to locate imperfections.

To compare the as found stent to the CAD model, images of the stent are obtained and the edges of the stent, which represent the form of the stent, are extracted. As discussed further below, imaging of the stent is best done utilizing a line camera based system to obtain a flat "unrolled" view of the part. Then, section-by-section, the edges from the as-measured stent are over-laid and best fit to the corresponding section of the CAD model. The deviation magnitude can be used as pass/fail criteria.

This section-by-section system can utilize a pattern-based approach as previously described in prior patents, or a given point or points on the stent pattern can be given and matched from the CAD model to the extracted data representing the edges of the stent. Between these reference points, the system tracks along both the CAD model and as-measured data to find deviations.

Typical defects that need to be found are gouges or sharp edges. However, since stents are flexible, the misalignment between as-found edges and a CAD model could be simply from this flexibility. Therefore, to account for misalignment, the edge data of the stent is typically warped to the CAD model or vice versa, prior to the deviation analysis. Warping of the data is described further below.

Figure 1:
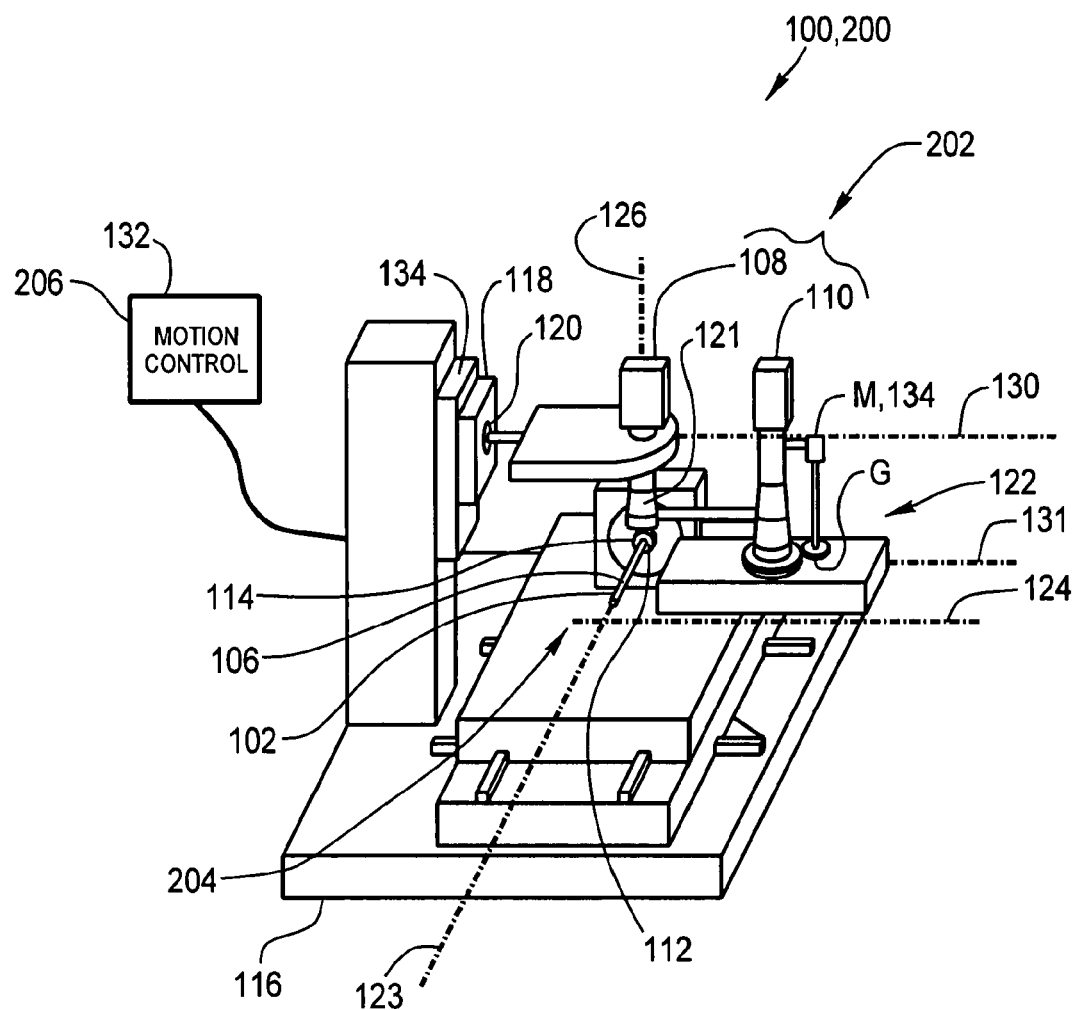
FIG. 1 is a front isometric view of an apparatus for capturing images of longitudinal surfaces and sidewalls of cut tubes according to some embodiments of the disclosed subject matter.
Figure 2:
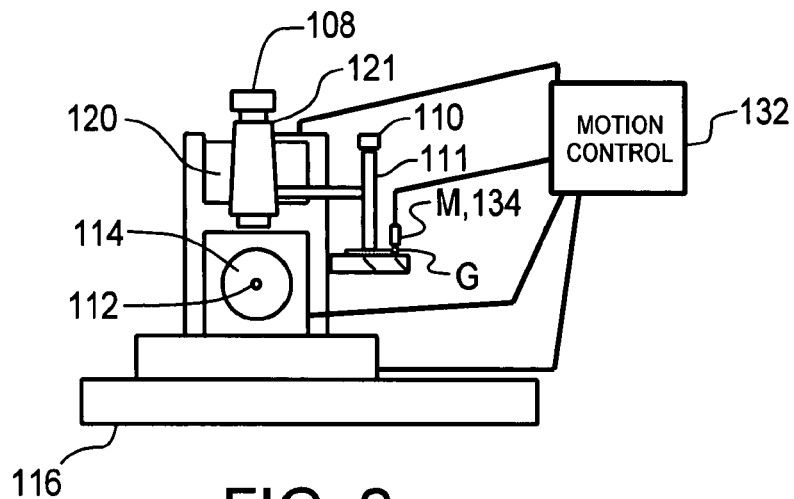
FIG. 2 is a side section view and schematic of an apparatus for capturing images of longitudinal surfaces and sidewalls of cut tubes according to some embodiments of the disclosed subject matter.
Figure 3:
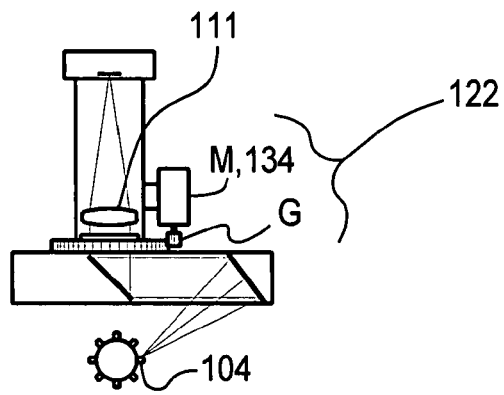
FIG. 3 is an enlarged partial section view of an area camera according to some embodiments of the disclosed subject matter.

Referring now to the figures and in particular to FIGS. 1-3, one embodiment of the disclosed subject matter is an apparatus 100 for capturing images of longitudinal surfaces 102 and sidewalls 104 of a cut tube such as a stent 106. Apparatus 100 includes a line camera 108, a rotatable, 360-degree area camera 110, a mandrel 112 and a drive 114, a multi-axis motion stage 116, a vertical motion stage 118, and a rotating motion stage 120.

Line camera 108 is configured to capture images of longitudinal surfaces 102 of stent 106. Line camera 108, which includes a lens 121, is similar to those described in U.S. Pat. No. 6,660,403, which is hereby incorporated by reference as if disclosed herein in its entirety.

Area camera 110 is typically, but not always, joined with line camera 108. Area camera 110 is configured to capture images of sidewalls 104 of stent 106. Because stent 106 can have many intricate features with closely cut sidewalls 104, area camera 110 typically, but not always, includes camera 110 in combination with a lens 111. A rotating mechanism 122, which can include gears G and a motor M, allows camera 110 to be rotated so that the stent can be viewed from multiple angles. A lens such as those used for 360-degree ball grid array inspection provides the ability to view stent 106 from any of 360 degrees around a circle.

Mandrel 112 and drive 114 are adapted to hold and axially rotate stent 106 about a Y-axis 123 for positioning the stent with respect to line camera 108 and area camera 110.

Multi-axis motion stage 116, which generally serves as a support surface for mandrel 112 and drive 114, is adjusted for moving the mandrel, drive, and stent 106 along an X-axis 124 and along Y-axis 123 for positioning the mandrel, drive, and cut tubes with respect to line camera 108 and area camera 110.

Vertical motion stage 118 is used to move line camera 108 and area camera 110 vertically along a Z-axis 126 for positioning the line camera and the area camera with respect to stent 106.

Figure 4:
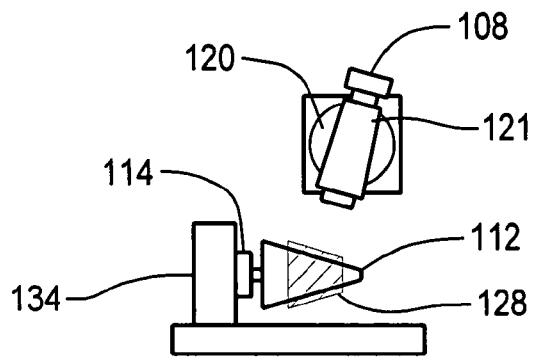
FIG. 4 is an enlarged partial section view of a line camera according to some embodiments of the disclosed subject matter.

Referring now to FIG. 4, stents such as stent 106 are also manufactured in a tapered configuration, i.e., shaped like a cone 128. Rotating motion stage 120 is used to rotate line camera 108 and area camera 110 substantially about an X'-axis 130 for positioning the line camera and the area camera with respect to stent 106. In this fashion, stent 106 can be in focus across an entire image of line camera 108. Alternatively the rotational stage holding stent 106, i.e., multi-axis motion stage 116, could itself be configured to rotate around an X"-axis 131 to achieve the same geometry.

Figure 5:
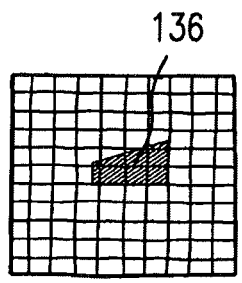
FIGS. 5-7 are images of a tapered stent captured using a line camera according to some embodiments of the disclosed subject matter.
Figure 6:
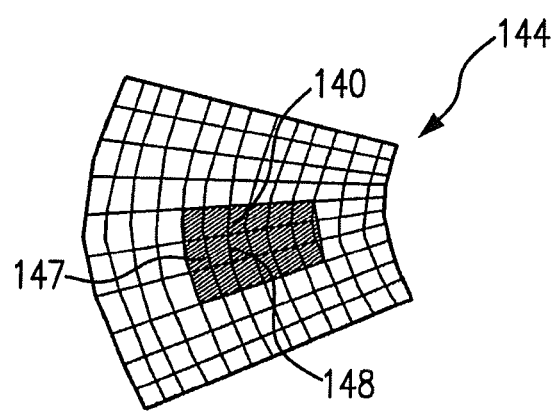
Figure 7:
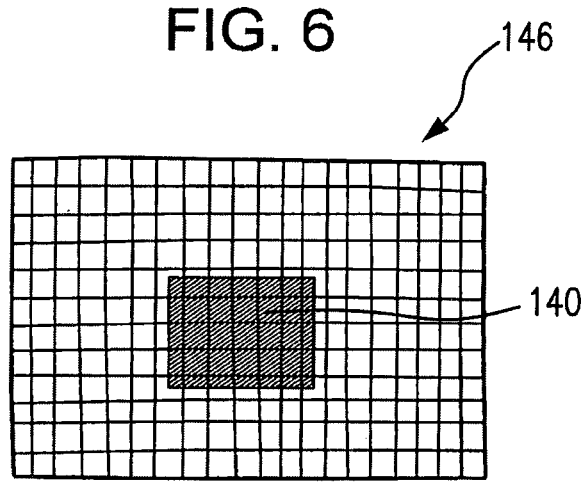

Referring now to FIGS. 5-7, in FIG. 5, the output 136 from line camera 108 of a rectangle cut into a tapered tube is illustrated. As shown in FIG. 6, the geometric distortion is corrected because the pixel 140 size changes based on the longitudinal position along the taper. Then, as illustrated in FIG. 7, the distorted shapes of the pixels are corrected into square pixels 140 that can be more easily processed by commercially available image processing hardware and software.

When conventionally imaged, the pixels 140 of the images captured of cone 128 no longer have a square or rectangular shape. They are more trapezoidal with slightly curved top 147 and bottom 148 edges. Further, the width of the pixels 140 varies based on the diameter of a stent at that longitudinal location. In the flat view of the image, a polar pixel 144 representation is created. By allowing for adjustment of line camera 108 in this fashion, the polar based pixel 144 system can be mapped to a Cartesian system 146 prior to image processing thereby facilitating the use of image processing hardware and software, which generally only works on rectangular or square pixels.

As schematically illustrated in FIG. 2, in some embodiments, apparatus 100 can include a motion control system 132 for controlling multi-axis motion stage 116, vertical motion stage 118, rotating motion stage 120, and rotating mechanism 122. Motion control system 132 can include a personal computer or similar device (not shown) for running a computerized program (not shown) that interacts with motors 134 that control each of stages 116, 118, and 120 based on predetermined parameters.

Referring again to FIGS. 1-3 and FIG. 8, another aspect of the disclosed subject matter is a system 200 for inspecting longitudinal surfaces 102 and sidewalls 104 of stent 106. System 200 includes a camera module 202, a tube positioning module 204, a motion control module 206, and an analysis module 208.

Camera module 202 includes line camera 108 and area camera 110. Line camera 108 is configured to capture images of longitudinal surfaces 102 of stent 106 and area camera 110 is configured to capture images of sidewalls 104 of the stent.

Tube positioning module 204 includes mandrel 112 and drive 114, which are adapted to hold and axially rotate stent 106 about a first axis 123, a multi-axis motion stage 116 for moving the mandrel, drive, and stent along the first axis and along a second axis 124, and a vertical motion stage 118 for moving line camera 108 and area camera 110 along a Z-axis 126.

Motion control module 206 controls multi-axis motion stage 116 and vertical motion stage 118 to position stent 106 with respect to line and area cameras 108 and 110, respectively. Motion control module 206 can also include a rotating motion stage 120 for rotating line camera 108 and area camera 110 about a second axis 130.

Analysis module 208 compares images of longitudinal surfaces 102 and sidewalls 104 of stent 106 to images of longitudinal surfaces and sidewalls of a template cut tube (not shown).

Figure 8:
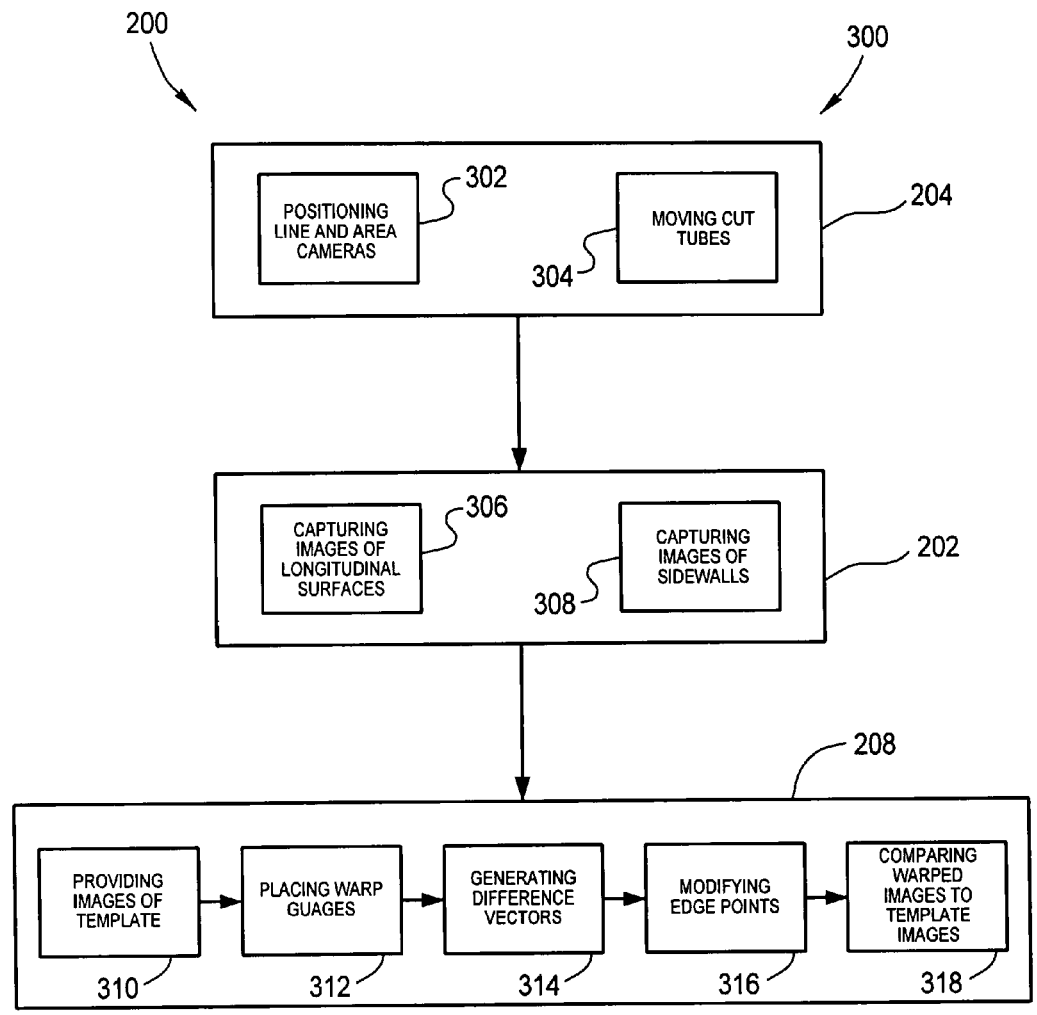
FIG. 8 is a chart of a method of inspecting longitudinal surfaces and sidewalls of cut tubes according to some embodiments of the disclosed subject matter.

Referring now to FIG. 8 and FIG. 1 (with respect to axes), another aspect of the disclosed subject matter is a method 300 of inspecting longitudinal surfaces and sidewalls of a cut tube or stent. At 302, method 300 includes positioning a line camera and an area camera for capturing images of the cut tubes. In some embodiments, the line camera and the area camera are positioned by moving them along a Z-axis. In some embodiments, the line camera and the area camera are positioned by rotating the line camera and the area camera substantially about an X'-axis. At 304, the cut tubes are moved with respect to the line and area cameras for capturing images of the cut tubes. In some embodiments, the cut tubes are moved by rotating them about a Y-axis. In some embodiments, the cut tubes are moved by moving them along at least one of X and Y-axes. At 306, images of the longitudinal surfaces of the cut tubes are captured using the line camera. At 308, images of the sidewalls of the cut tubes are captured using the area camera. At 310, images of the sidewalls and longitudinal surfaces of a template cut tube are provided. At 312, warp gauges are placed at positions on the sidewalls and longitudinal surfaces of the template cut tube. At 314, difference vectors between the positions of the warp gauges and comparable positions of the captured images of longitudinal surfaces and sidewalls of the cut tubes are generated. At 316, edge points of longitudinal surfaces and sidewalls of the cut tubes are modified based on a weighted average of a nearest warp gauge thereby generating warped images of the sidewalls and longitudinal surfaces of the cut tubes. At 318, the warped images of longitudinal surfaces and sidewalls of the cut tubes are compared to the images of the sidewalls and longitudinal surfaces of the template cut tube.

As discussed in method 300, for stents produced using flexible materials, it is preferred that the edge data of the stent be warped to the CAD model or template stent to account for any misalignment between the stent and CAD model/template stent.

Figure 9:
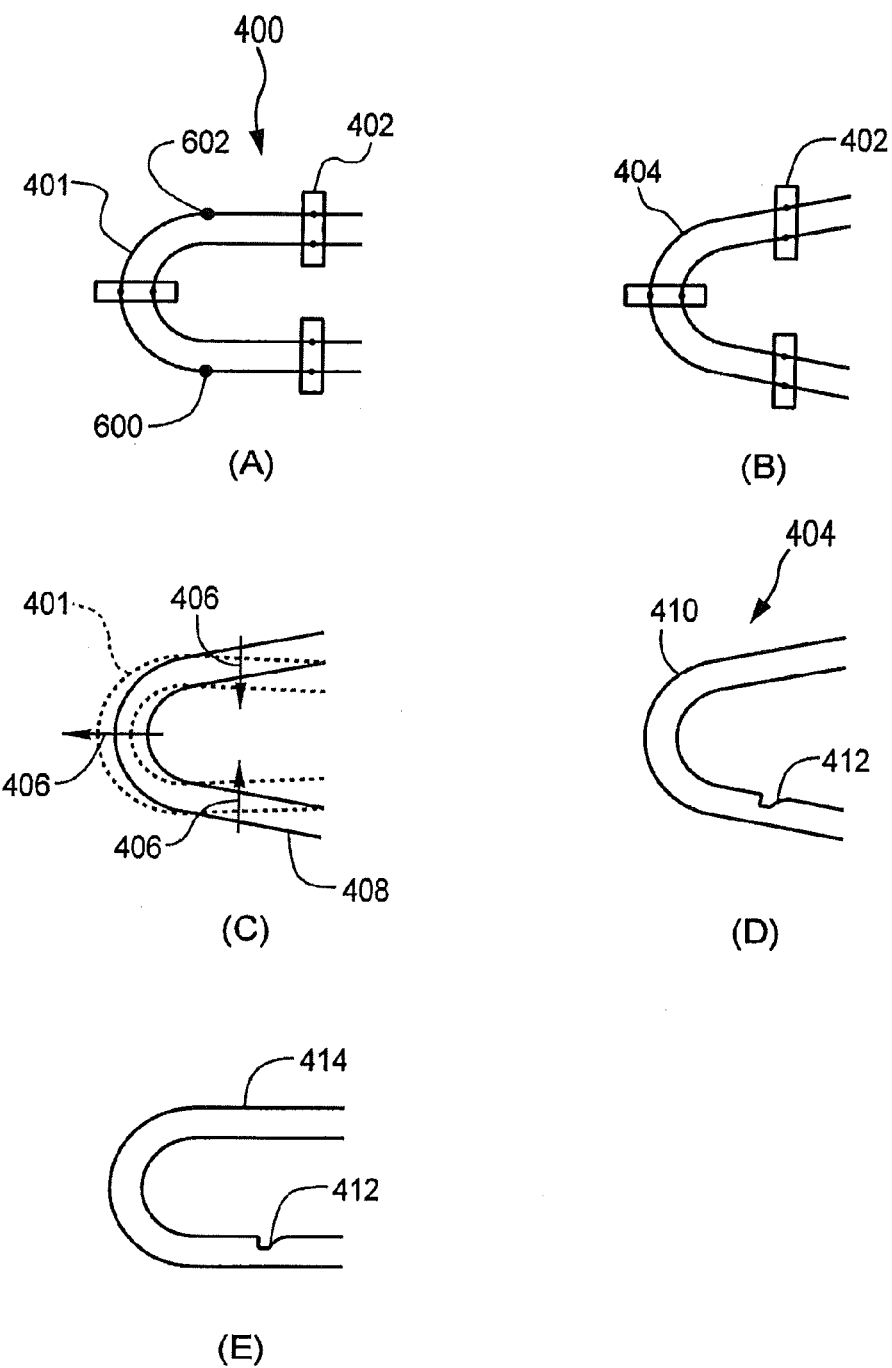
FIGS. 9A-9E are schematic illustrations of the warping of a stent image to a CAD model according to some embodiments of the disclosed subject matter.

Referring now to FIGS. 9A-9E, warping is performed by first creating or obtaining a CAD model 400 that represents an idealized representation of a stent section 401 that requires inspection. As illustrated in FIGS. 9A and 9B, this representation can be in the form of a .bmp format image or other image file and may be referred to as a template stent 401. On template stent 401, a number of warp gauges 402 are placed to find the locations of the actual edges of an as-inspected stent 404. Warp gauges 402 look like typical video edge detection tools, however, as illustrated in FIG. 9C, their function is to generate difference vectors 406 between the position of the stent feature as found in an as-inspected image 408 of stent 404 and the ideal position as represented by template stent 401.

Once all the warp gauges 402 generate difference vectors 406, the edge points, on a point-by-point basis, can be modified based on a weighted average of the nearest warp gauges. As long as the warp gauges are not placed too densely on the template stent, this technique will have the effect of bending the as-found data to match the CAD model/template stent on a low frequency basis. However, the critical defects, which are at a higher frequency, e.g., more abrupt changes, are retained and can be seen as deviations.

As shown in FIG. 9D, prior to warping, an image 410 of stent 404 reveals a defect 412. As shown at FIG. 9E, after warping image 410 to CAD model 400, a warped image 414 of stent 404 still reveals defect 412.

In the case of stent features such as struts, one would like to preserve the dimension across the strut but still warp this feature to a CAD model. To do this, the warp tool can tie together the difference vector on either side of the strut and move the strut equally on both edges.

In expanding on the concept of differentiating low frequency from high frequency deviations, the CAD model comparison method can be used to find defects that are within the nominally produced tolerance range of the part. The string of deviation values along a given edge are treated as a function and the first derivative of that function is taken to find the rates of change from one deviation value to the next. While the actual deviations may stay within the tolerance bounds, if there are sharp changes in these values, it indicates a potential flaw within a stent.

Figure 10:
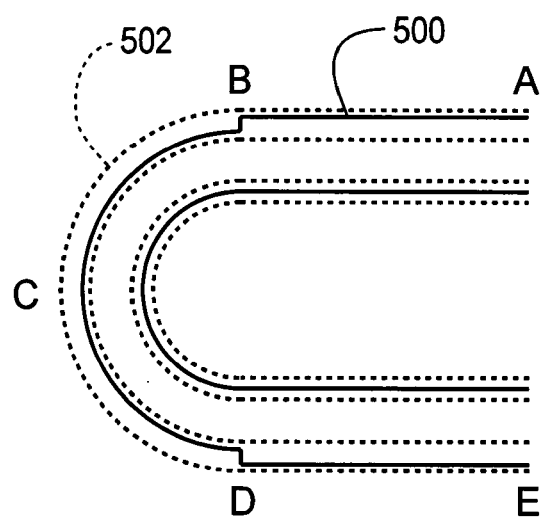
FIGS. 10A-10C are schematic illustrations and graphs of a defective stent that is within prescribed tolerance limits according to some embodiments of the disclosed subject matter.
Figure 10:
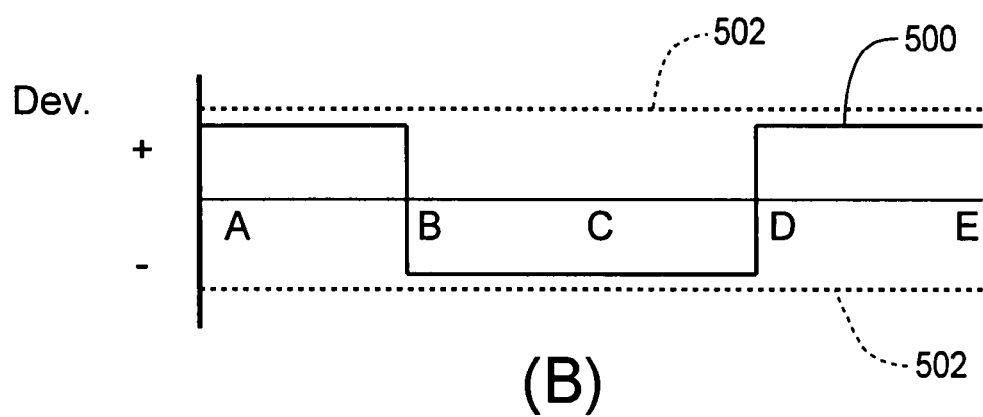
Figure 10:
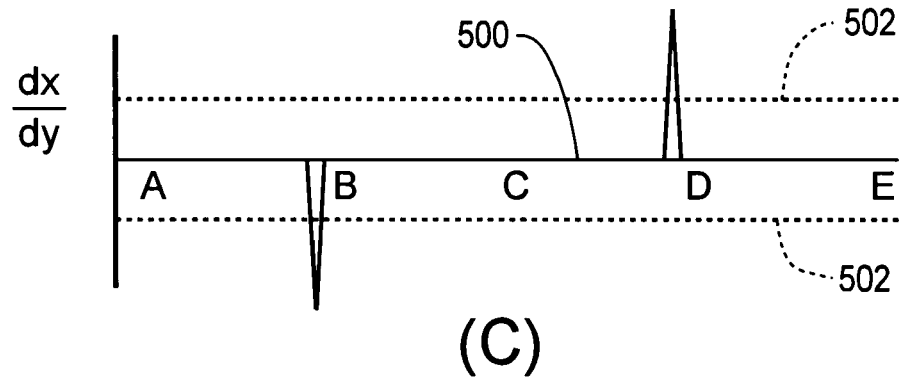

Referring now to FIGS. 10A-10C, an as-measured stent 500, which conforms to tolerance restrictions (as defined by dashed lines 502), is illustrated. However, as revealed at points B and D, stent 500 is defective. FIG. 10B illustrates how the defects in stent 500 stay within the tolerance bounds. FIG. 10C shows that the first derivative of the deviation values along stent 500 reveal spikes in the data at points B and D that represent part defects. The tolerance bands can be set to accept gently changing shapes of a stent while rejecting high frequency deviations or spikes in the data.

Techniques are well known for methods to extract the best-fit curve or line from a set of data. It is reasonable to obtain a set of edges representing a given stent from an image such as a .bmp and use those edges to define a CAD model such as a .dxf. However, to create a template stent or CAD model from actual parts, it would be favorable to capture data from an assortment of representative parts rather than just one part.

To do this, image files are scanned and generated for a representative sample, e.g., 30 pieces of a part. From each part, edge data points that represent the part are generated. From one of them, a first CAD model or template stent is generated. A least-squares regression or other well-known technique for best fitting is used to best fit the data to the model. Further data sets are iteratively introduced, each time best fitting them to the CAD model. This will effectively load all the data sets on top of each other.

Each element of the CAD model is allowed, such as line or arc, to adjust by translation or rotation to best fit to the conglomerate set of data. The only constraint is that adjacent elements must still join at the end of the fitting iterations. Once this is done, a template that represents the average of the sample of parts had been generated. To further refine this model, each of the subsequent data sets can again be best fit to this newly adjusted CAD model to create an even better registered set of data. Once again, each element of the CAD model can be allowed to adjust by translation or rotation to best fit to the more precisely registered conglomerate set of data. This can be repeated iteratively until the improvements in deviation are diminishingly small.

One common problem of automatic best-fit routines is that they can find and stick with a local optimization minimum that is not the absolute best fit. Further, these techniques can be computationally intensive due to the high number of rotation and translation increments that can be tried. To deal with these issues, two alignment points can be placed on both the CAD model and two similar alignments points corresponding to the same positions on the part images from which the part edges are extracted. Referring again to FIG. 9A, one of the alignment points is an "anchor" point 600 and the other is a "skew" point 602.

In operation, the system first translates the anchor point and all other corresponding points in the data set such that the anchor point in the data lies on top of the anchor point in the model. Then based on the difference in angles between the skew points of model and data set, the points of the data set are rotated about the anchor point such that the skew point of the data set lies along a line defined by the skew and anchor points of the model. This brings a very reasonable alignment between model and data in just two operations. From here, the traditional least squares and other methods can be employed to find a very precise best fit.

All of the above techniques are useful for finding defects of parts in a profile view. As described above, to find defects along the sidewalls of a stent, a different technique is employed. The operator is presented with a view of the stent in the unrolled format and can manually define points to which a sidewall inspection is required. In the case of nitinol stents, the corners where two struts join are high stress areas and are likely to require a sidewall inspection. The defined points for inspection can be placed directly on the image or within a pattern section that is repeated throughout the part. Alternatively, the operator can require all sections of the sidewall to be inspected and ask the machine to automatically place inspection points on the image.

To improve system throughput, light-emitting diodes (LEDs) can be used in a pulse mode to freeze the motion of the camera to drive from one inspection location to the next without stopping. The area of the image that contains the sidewall to be inspected can be calculated from the original unrolled scan. This information can be passed to the camera so that only the meaningful pixels are transmitted to the image-processing host or this information can be passed to the image processing host directly and used as a mask to limit the number of pixels that need to be analyzed.

If a greater depth of field than the image provides is required, the viewing vector can be calculated and a number of images can be acquired each at a slightly different distance to the part. These images can be converged into a single image of extended depth of focus using well know techniques from commercially available software. This allows for the calculation of the appropriate optical vector in which to take these multiple images from the geometry originally derived from the unrolled image.

In addition to the use described above, a sidewall viewing camera according to the disclosed subject matter can also be used in conjunction with found potential defects on the original unrolled image of the stent to take a closer look at a higher magnification to verify the potential defect.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. An apparatus for capturing images of longitudinal surfaces and sidewalls of cut tubes, said apparatus comprising:
   a line camera, said line camera being configured to capture images of longitudinal surfaces of the cut tubes;
   a rotatable, 360 degree area camera joined with said line camera, said area camera being configured to capture images of sidewalls around 360° of the cut tubes;
   a mandrel and drive adapted to hold and axially rotate the cut tubes about a Y-axis for positioning the cut tubes with respect to said line camera and said area camera;
   a multi-axis motion stage for moving the mandrel, drive, and cut tubes along an X-axis and along said Y-axis for positioning the mandrel, drive, and cut tubes with respect to said line camera and said area camera;
   a vertical motion stage for moving said line camera and said area camera along a Z-axis for positioning said line camera and said area camera with respect to the cut tubes; and
   a rotating motion stage for rotating said line camera and said area camera substantially about an X'-axis for positioning said line camera and said area camera with respect to the cut tubes.

2. An apparatus according to claim 1, further comprising a motion control system for controlling said multi-axis motion stage, said vertical motion stage, and said rotating motion stage.

3. An apparatus according to claim 1, wherein said line camera is configured to capture images of the longitudinal surfaces of a stent.

4. An apparatus according to claim 1, wherein said area camera is configured to capture images of the sidewalls surfaces of a stent.

5. An apparatus according to claim 1, further comprising a rotating mandrel stage for rotating said mandrel, drive, and cut tubes about an X"-axis for positioning said mandrel, drive, and cut tubes with respect to said line and area cameras.

6. An apparatus according to claim 1, further comprising a rotating mechanism for rotating said area camera.

7. A system for inspecting longitudinal surfaces and sidewalls of cut tubes, said system comprising:

a camera module including a line camera and a rotatable, 360 degree area camera, said line camera being configured to capture images of longitudinal surfaces of the cut tubes and said area camera being configured to capture images of sidewalls around 360° of the cut tubes;

a tube positioning module including a mandrel and drive adapted to hold and axially rotate the cut tubes about a first axis, a multi-axis motion stage for moving the mandrel, drive, and cut tubes, along said first axis and along a second axis, and a vertical motion stage for moving said line camera and said area camera along a Z-axis;

a motion control module for controlling said multi-axis motion stage and said vertical motion stage to position the cut tubes with respect to said line and area cameras; and an analysis module for comparing said images of the longitudinal surfaces and sidewalls of the cut tubes to images of longitudinal surfaces and sidewalls of a template cut tube.

8. A system according to claim 7, wherein said motion control module includes a rotating motion stage for rotating said line camera and said area camera about a second axis, wherein said second axis is adapted to be positioned substantially perpendicular to said first axis.

9. A system according to claim 7, wherein said line camera is configured to capture images of the longitudinal surfaces of a stent.

10. A system according to claim 7, wherein said area camera is configured to capture images of the sidewalls surfaces of a stent.

11. A system according to claim 7, wherein said camera module includes a rotating mechanism for rotating said area camera.

12. The system of claim 7 wherein said analysis mode warps said images to match templates and then compares said warped images to template images of said longitudinal sides and sidewalls.

13. A method for inspecting longitudinal surfaces and sidewalls of cut tubes having a conical shape, said method comprising: providing a line camera to capture trapezoidal pixel images of longitudinal surfaces of said cut tube; providing an area camera to capture images of sidewalls of said tube; reconfiguring said trapezoidal images to square pixels for analysis: and subsequent to said reconfiguring step, utilizing a computer to compare said images of longitudinal surfaces and said images of sidewalls with images of longitudinal surfaces and images of sidewalls of a template cut tube, wherein a non-transitory computer readable recording medium having housed thereon has a computer program that, compares an image of said cut tube with that cut tube's CAD model and locates imperfections on longitudinal surfaces and sidewalls of the cut tube, said computer program further compensates for general and for low frequency deviations in the comparison between said cut tube and the CAD model in a section-by-section overlay and best-fit of corresponding sections of a CAD data set and an actual data set so that defects in said cut tube are indicated by deviation from a minimum amplitude or slope of said low frequency deviations.

\* \* \* \* \*